US00PP36450P2

(12) United States Plant Patent
Miller

(10) Patent No.: US PP36,450 P2
(45) Date of Patent: Feb. 11, 2025

(54) ***CALIBRACHOA* PLANT NAMED 'CBRZ0048'**

(50) Latin Name: *Calibrachoa hybrida*
Varietal Denomination: CBRZ0048

(71) Applicant: SYNGENTA CROP PROTECTION AG, Basel (CH)

(72) Inventor: Baylee Miller, Gilroy, CA (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/383,536

(22) Filed: Oct. 25, 2023

(51) Int. Cl.
*A01H 5/02* (2018.01)
*A01H 6/82* (2018.01)

(52) U.S. Cl.
USPC ..... Plt./413

(58) Field of Classification Search
USPC ..... Plt./413
See application file for complete search history.

*Primary Examiner* — Susan McCormick Ewoldt
*Assistant Examiner* — Zachariah Allan Kay
(74) *Attorney, Agent, or Firm* — Dale Skalla

(57) ABSTRACT

A new *Calibrachoa* plant named 'CBRZ0048' particularly distinguished by medium sized orange flowers with a red eye, begins to flower during 10.5 hours of daylength, has a mounding to semi-trailing plant habit, and grows moderately fast relative to other *Calibrachoa* varieties and exhibits a spreading habit.

1 Drawing Sheet

Figure 1:
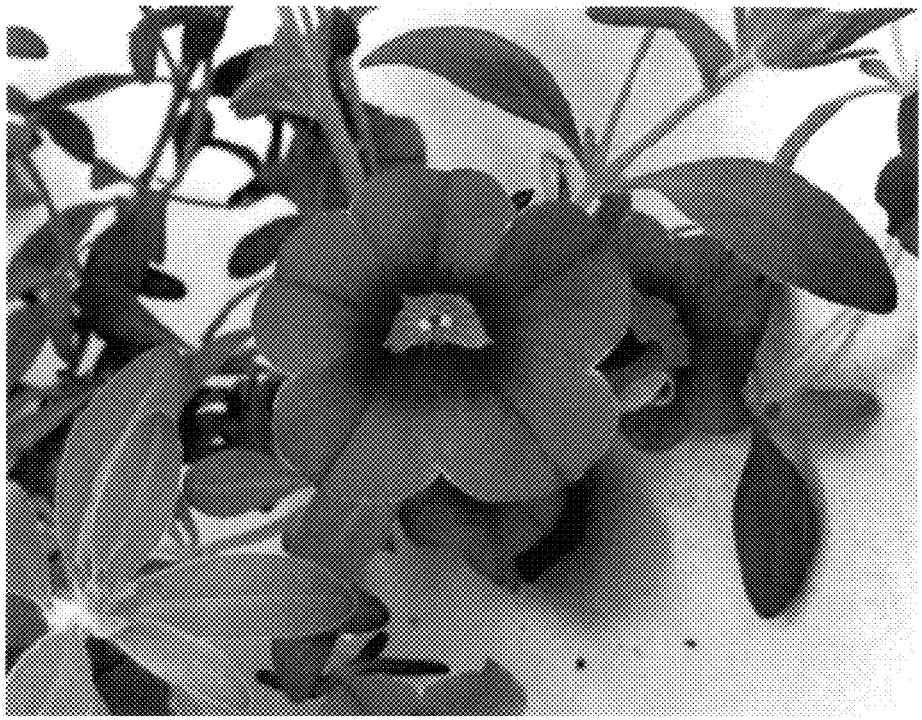

Latin name of the genus and species of the plant claimed: *Calibrachoa hybrida.*

Varietal denomination: 'CBRZ0048'.

BACKGROUND OF THE NEW PLANT

The present invention comprises a new *Calibrachoa*, botanically known as *Calibrachoa hybrida*, and hereinafter referred to by the variety name 'CBRZ0048'.

'CBRZ0048' is a product of a planned breeding program. The new cultivar has medium sized orange flowers with a red eye, begins to flower during 10.5 hours of daylength, has a mounding to semi-trailing plant habit, and grows moderately fast relative to other *Calibrachoa* varieties and exhibits a spreading habit.

'CBRZ0048' originated from a hybridization made in July 2018 in a greenhouse in Gilroy, California. The female parent was an unpatented commercial variety 'Callie Medium Yellow' with yellow color with no eye, small to medium sized flowers, and is later flowering.

The male parent of 'CBRZ0048' was an unpatented proprietary plant known as 'CALCC4308-8V' having a light orange flower color with medium orange eye, and has a more upright plant habit.

The resulting seeds were sown in October 2018 and 'CBRZ0048' was selected as one flowering plant within the progeny of the stated cross in June 2019 in a controlled environment in Gilroy, California.

The first act of asexual reproduction of 'CBRZ0046' was accomplished when vegetative stem cuttings were propagated from the initial selection in June 2019 in a controlled environment in Gilroy, California.

BRIEF SUMMARY OF INVENTION

Horticultural examination of plants grown from cuttings of the plant initiated in the summer of 2019, and continuing thereafter, has demonstrated that the combination of characteristics as herein disclosed for 'CBRZ0048' are firmly fixed and are retained through successive generations of asexual reproduction.

'CBRZ0048' has not been observed under all possible environmental conditions. The phenotype may vary significantly with variations in environment such as temperature, light intensity, and day length.

A Plant Breeder's Right for this cultivar has not yet been applied for. 'CBRZ0048' has not been made publicly available prior to the effective filing date of this application, notwithstanding any disclosure that may have been made less than one year prior to the effective filing date of this application by the inventor or another who obtained 'CBRZ0048' directly from the inventor.

The following traits have been repeatedly observed and are determined to be basic characteristics of the new variety. The combination of these characteristics distinguishes this *Calibrachoa* as a new and distinct variety.

TABLE 1

DIFFERENCES BETWEEN THE NEW VARIETY 'CBRZ0046' AND A SIMILAR VARIETY

| | 'CBRZ0048' | 'Balcaborim', U.S. Plant Pat. No. 31,572 |
|---|---|---|
| Flower pattern | Medium orange color with red eye | Medium orange color with no eye |
| Flower color fade | Flower color fades slightly to a peachy color as flowers age | Flower color fades slightly to a yellow-orange color as flowers age |
| Plant habit | Semi trailing to trailing | Trailing |

BRIEF DESCRIPTION OF THE PHOTOGRAPHS

The accompanying photographic drawing shows typical flower and foliage characteristics of 'CBRZ0048' with colors being as true as possible with an illustration of this type.

Figure 2:
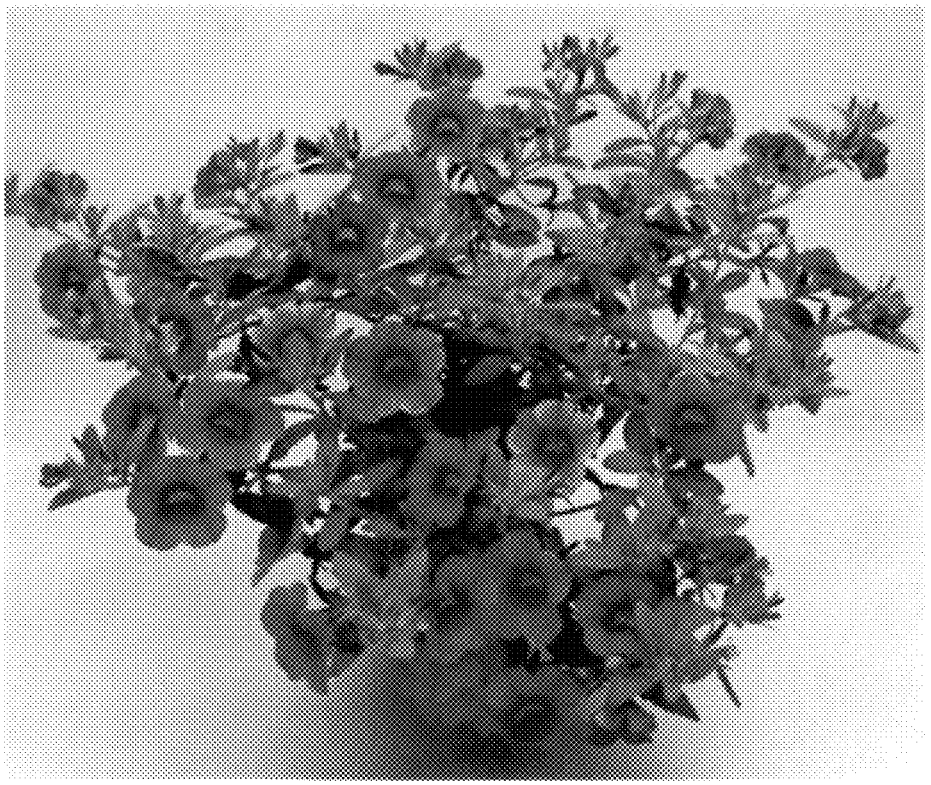

The photographic drawings show in FIG. 1 a close-up of the flowers and in FIG. 2 a flowering plant of the new variety.

The aforementioned photographs were taken in May 2023 in a greenhouse in Andijk, The Netherlands.

DETAILED BOTANICAL DESCRIPTION

The measurements and observations were made in October 2023 in Gilroy, California on plants grown outdoor in 35 cm containers. Plants were about 16 weeks of age.

Color references are made to The Royal Horticultural Socicty Colour Chart (R.H.S.) 2015.

Plant:

*Form, growth and habit*.—Moderately compact and mounding, trailing.
*Plant height*.—16 inches.
*Plant height* (*inflorescence included*).—17 inches.
*Plant width*.—30 inches.
*Quantity of main branches*.—15-20.
*Quantity of secondary branches*.—6-8 per basal branch.
*Time to produce a flowering plant*.—9-10 weeks for a 12 cm pot (from planting of rooted cuttings).

Roots:

*Number of days to initiate*.—18-21 days at about 22° C.
*Number of days to produce a rooted cutting*.—21-24 days at 22° C.
*Type*.—Fibrous.
*Color*.—RHS 158D.

Stem:

*Color of stem*.—RHS 146C.
*Length of stem*.—Approximately 15 cm.
*Diameter*.—0.2 cm.
*Length of internodes*.—1.5-2.5 cm.
*Texture*.—Smooth, small fine hairs.

Foliage:

*Immature leaf, color of upper surface*.—RHS 147A.
*Immature leaf, color of lower surface*.—RHS 147B.
*Mature leaf, color of upper surface*.—RHS 147A.
*Mature leaf, color of lower surface*.—RHS 147B.
*Leaf blade, length*.—3.0 cm.
*Leaf, width*.—1.4 cm.
*Shape*.—Elliptical.
*Base shape*.—Attennuate.
*Apex shape*.—Obtuse.
*Margin*.—Entire.
*Texture*.—Small fine hairs.
*Color of veins, upper surface*.—RHS 146B.
*Color of veins lower surface*.—RHS 146B.
*Petiole color*.—RHS 146C.
*Petiole length*.—0.0-0.1 cm.
*Diameter of petiole*.—0.2 cm.
*Texture*.—Smooth.

Inflorescence:

*Type*.—Flowers solitary in upper leaf axis and slanting upright or outwards.
*Quantity of inflorescences per plant*.—Approximately 120.
*Lastingness of individual flowers*.—About 7-9 days.
*Fragrance*.—None.
*Duration of flowering*.—Continuous flowering throughout the summer.

Pedicel:

*Color of pedicel*.—RHS 146B.
*Length of pedicel*.—1.5-2.3 cm.
*Diameter of pedicel*.—1.0 mm.
*Texture of pedicel*.—Glandular hairs of various sizes.

Flower:

*Immature flowers, corolla upper surface*.—RHS 42A, towards base RHS 46B.
*Immature flowers, corolla lower surface*.—RHS 42A.
*Mature flowers, color upper surface*.—RHS 31A, towards base RHS 46B.
*Mature flowers, color lower surface*.—RHS 31A.
*Flower horizontal diameter*.—3.5 cm.
*Flower height* (*vertical*).—2.8 cm.
*Corolla tube length*.—About 1.3 cm.
*Petal apex shape*.—Rounded.
*Margin*.—Entire.
*Waviness of petals*.—Weak.
*Petal lobation*.—Moderate.
*Corolla texture*.—Smooth.
*Corolla tube color inside*.—RHS 14A with veins RHS N77B.
*Corolla tube color outside*.—RHS 14C with veins RHS 152B.

Bud (just before opening):

*Color at apex*.—RHS 70A.
*Length*.—2.5 cm.
*Width* (*upper end*).—1.2 cm.
*Shape*.—Oblong.

Calyx:

*Number of sepals*.—5.
*Color of sepals, adaxial or upper surface*.—RHS 147A.
*Color of sepals, abaxial or lower surface*.—RHS 147B.
*Length of sepals*.—14 mm.
*Width of sepals*.—3 mm.
*Sepal shape*.—Lanceolate.
*Apex shape*.—Acute.
*Margins*.—Entire.
*Texture*.—Glandular hairs of various sizes.

Reproductive organs:

*Pistil*.—1.
*Length*.—1.3 cm.
*Style color*.—RHS 145C.
*Style length*.—0.8-0.9 cm.
*Stigma color*.—RHS N144C.
*Number of stamens*.—5.
*Color of filaments*.—RHS 4D.
*Length filaments*.—0.9 cm.
*Color of pollen*.—RHS 14C.
*Pollen amount*.—Abundant.
*Fertility/seed set*.—Not observed on this hybrid to date.
*Disease/pest resistance*.—Not observed on this hybrid to date.

What is claimed is:

1. A new and distinct variety of *Calibrachoa* plant named 'CBRZ0048' substantially as illustrated and described herein.

* * * * *